United States Patent [19]

Shigematsu et al.

[11] 4,162,315

[45] Jul. 24, 1979

[54] AGRICULTURAL FUNGICIDAL COMPOSITION

[75] Inventors: Taichiro Shigematsu; Tetsuya Shibahara; Makoto Nakazawa, all of Yokohama; Masayuki Tomida, Sagamihara; Toshio Munakata, Tokyo, all of Japan

[73] Assignee: Mitsubishi Chemical Industries Limited, Tokyo, Japan

[21] Appl. No.: 810,999

[22] Filed: Jun. 29, 1977

Related U.S. Application Data

[62] Division of Ser. No. 638,761, Dec. 8, 1975, Pat. No. 4,049,820.

[30] Foreign Application Priority Data

Dec. 13, 1974 [JP] Japan ................. 49-143183

[51] Int. Cl.$^2$ ..................... A01N 9/22; C07D 487/04
[52] U.S. Cl. ..................................... 424/250; 424/269
[58] Field of Search ............................... 424/250, 269; 260/250 AC

[56] References Cited

U.S. PATENT DOCUMENTS 3,925,379  12/1975  Bredon et al. ................. 260/250 AC

FOREIGN PATENT DOCUMENTS 2149923  4/1972  Fed. Rep. of Germany.
2429042  6/1973  Fed. Rep. of Germany.

OTHER PUBLICATIONS

Agr. Biol. Chem., vol. 36, No. 2, pp. 318-323, (1972).
Agr. Biol. Chem., vol. 35, No. 11, pp 1707-1719, (1971).

Primary Examiner—Mark L. Berch
Attorney, Agent, or Firm—Bierman & Bierman

[57] ABSTRACT

There is disclosed a fungicide comprising, as the active ingredient, a 1,2-alkylene-4-(3',5'-dichlorophenyl) urazole derivative suitable for preventing various diseases of plants including fruit trees, vegetables, rice plant and beans.

8 Claims, No Drawings

AGRICULTURAL FUNGICIDAL COMPOSITION

This is a Rule 60 divisional application of copending Ser. No. 638,761 filed on Dec. 8, 1975 now U.S. Pat. No. 4,049,820 and which claims the priority of Japanese patent application No. 143183/1974 filed on Dec. 13, 1974.

This invention relates to an agricultural fungicide.

A wide variety of agricultural fungicides have been developed, but some of them are not used because they cause ecological pollution.

We have conducted intensive studies to find an agricultural fungicide which possesses a superior fungicidal effect but has low toxicity and have found that certain urazole derivatives satisfy these requirements.

Accordingly, this invention provides a novel agricultural fungicide which comprises, as an active ingredient, a 1,2-alkylene-4-(3',5'dichlorophenyl) urazole represented by the general formula:

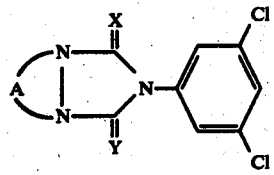

wherein A represents alkylene having 3 to 8 carbon atoms which may have branched methyl, and X and Y may be the same or different and represent oxygen and sulfur.

It has already been found that some of 1,2,4-substituted urazole derivatives have fungicidal, herbicidal and insecticidal activities. Compounds represented by the above general formula are novel and possess excellent fungicidal activity against a wide variety of plant diseases, but are nonpathogenic against the host plant and have no or little toxicity against humans and fishes.

The fungicide according to this invention is especially effective against rice sheath blight disease, Botrytis gray mold disease, rice brown spot disease, Sclerotinia rot and Alternaria leaf spot; in some cases, two or more diseases are prevented simultaneously.

The compounds which are suitable for this invention are prepared by various routes.

Route A

A solution of 1,2-alkylene-4-(3',5'-dichlorophenyl) urazole in a solvent, such as xylene or cumene is treated with phosphorus pentasulfide under reflux for a few hours to produce the mono- or di-thio derivative.

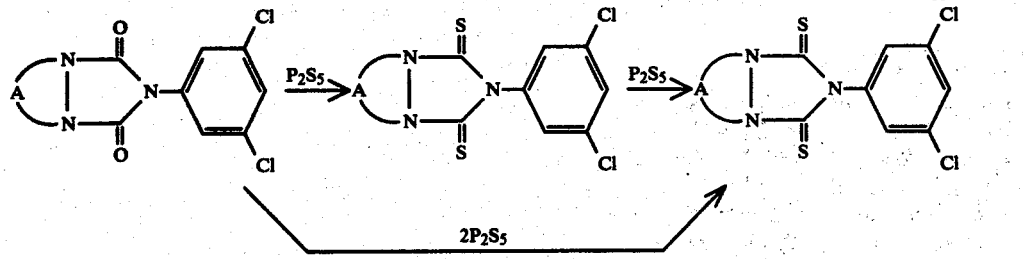

wherein A has the same meaning as above.

By varying the proportion of the reactants, monothio- or dithio-urazole is selectively prepared.

Route B

A diene compound and 4-(3',5'-dichlorophenyl) urazole are reacted in the presence of an oxidizing agent such as lead nitrate, lead acetate and $N_2O_4$ to effect a Diels-Alder reaction to prepare N-3',5'-dichlorophenyl-1,2,3,6-tetrahydro pyridazine 1,2-dicarboxylic imide which is then hydrogenated in a solvent such as ethylacetate, tetrahydrofuran, acetic acid or alcohol in the presence of a catalyst such as Pd-C and $Pt_2O$ to give the desired compound.

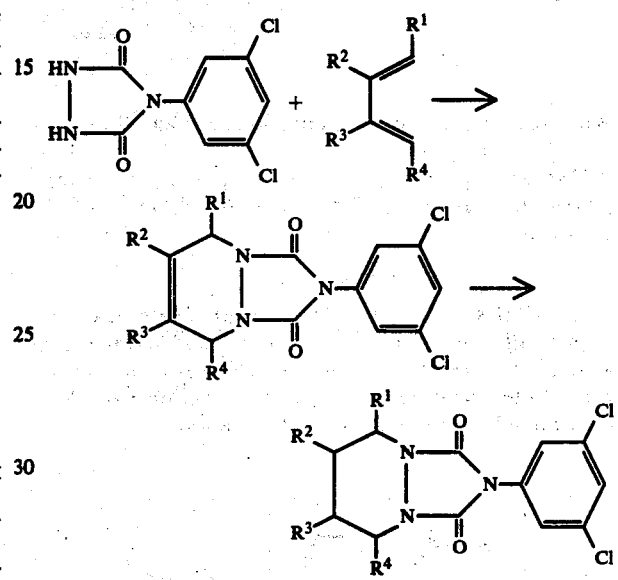

wherein $R^1$ to $R^4$ may be the same or different and represent hydrogen and methyl.

Route C

To a solution of 1,2-alkylene-1-alkoxycarbonyl hydrazine in a solvent such as benzene, toluene, xylene or cumene is added dropwise 3,5-dichlorophenyl isothiocyanate in a stoichiometric amount to produce 1,2-substituted 1-alkoxycarbonyl-2-(3',5'-dichlorophenyl thiocarbamoyl) hydrazine and the resulting reaction mixture is refluxed for from a few to ten-odd hours to obtain the desired monothiourazole product.

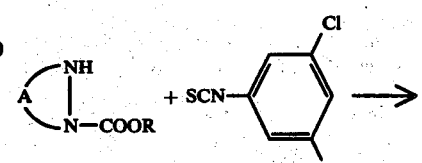

-continued

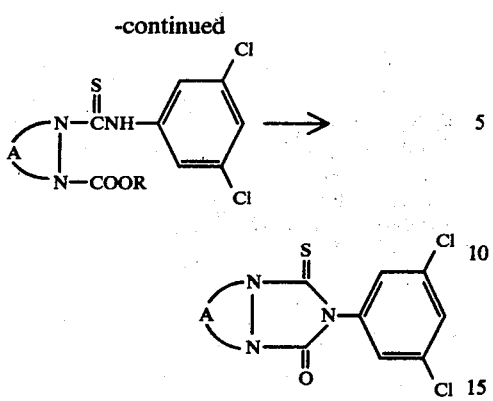

wherein A has the same meaning as above and R represents lower alkyl.

Dithiourazole derivatives are prepared by similar procedures using 1,2-substituted-1-alkylthiocarbonyl hydrazine.

Route D

A salt of 4-(3',5'-dichlorophenyl) urazole is reacted with an alkylene dihalide in a solvent such as water, an alcohol, dimethylformamide, tetrahydrofuran or benzene at a temperature of from room temperature to 200° C. for a half to a few hours with agitation.

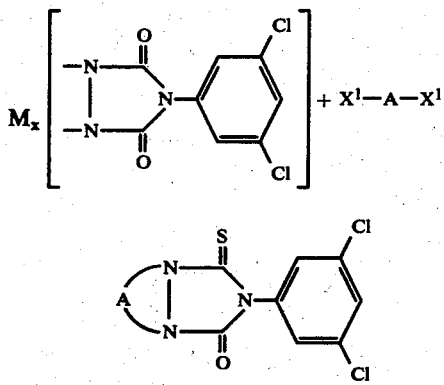

wherein A represents alkylene of 3 to 8 carbon atoms which may have branched methyl, $X^1$ represents halogen, M represents a monovalent or bivalent metal or amine, and X is 2 when M is monovalent; X is 1 when M is bivalent.

The preparation of the compound which may be used as active ingredient according to this invention will be explained in detail by means of the following Reference Examples.

Reference Example 1

To a suspension of 29 g of disodium 4-(3',5'-dichlorophenyl) urazole in 200 ml of dried N,N-dimethylformamide was added 26.4 g of 1,4-dibromopentane and the resulting mixture was refluxed for one hour with agitation. After removing N,N-dimethylformamide in vacuo, the residue was poured into 500 ml of water to give a solid material which was filtered and recrystallized from ethanol to obtain 23.2 g of 1,2-pentamethylene-4-(3',5'-dichlorophenyl) urazole, the yield being 74%.

Reference Example 2

Into a suspension of 2.85 g of 4-(3',5'-dichlorophenyl) urazole was absorbed 0.7 g of 1,3-butadiene and a solution of 6.7 g of lead tetraacetate in 100 ml of dichloromethane was added dropwise over 30 minutes to the suspension which was maintained at a temperature of from 0° to 5° C. by cooling with agitation. After continuing agitation for a further 2 hours, the dichloromethane was distilled off at a temperature below 30° C. in vacuo.

The residue was washed, in sequence, with each of 75 ml of water, 0.1N nitric acid, 0.1N aqueous sodium hydroxide and water and recrystallized from ethylacetate to obtain N-(3',5'-dichlorophenyl)-1,2,3,6-tetrahydropyridazine-1,2-dicarboxylic imide (the yield being 2.8 g and 82%).

The melting point was 167°-168° C. and the elementary assay as $C_{12}H_9N_3O_2Cl_2$ was:

|  | C(%) | H(%) | N(%) | Cl(%) |
|---|---|---|---|---|
| Calculation | 48.34 | 3.04 | 14.09 | 23.79 |
| Found | 48.31 | 3.01 | 14.25 | 23.82 |

Into a solution of 1.5 g of the product thus produced in 50 ml of ethylacetate was passed through hydrogen under a normal pressure in the presence of 0.1 g of 5% Pd-C catalyst until no absorption of hydrogen was detected. After removing the catalyst by filtration, the ethylacetate was distilled off in vacuo to obtain 1,2-pentamethylene-4-(3',5'-dichlorophenyl) urazole in an amount of 1.4 g, a yield of 95%.

Reference Example 3

A solution of 5.7 g of 1,2-trimethylene-4-(3',5'-dichlorophenyl) urazole (which was prepared according to procedures in Reference Example 1) and 4.4 g of phosphorus pentasulfide in 50 ml of xylene was heated under reflux for four hours with agitation. The reaction mixture was allowed to cool to precipitate solid material which was filtered out. The solvent was removed in vacuo and the residue was recrystallized from ethanol to obtain 1,2-trimethylene-4-(3',5'-dichlorophenyl) monothiourazole in an amount of 2.5 g, a yield of 41%.

Reference Example 4

Two grams (0.01 mole) of 3,5-dichlorophenyl isothiocyanate were added in small increments to a solution of 1.7 g of 1,2-pentamethylene-1-ethoxycarbonyl hydrazine with shaking, then 1,2-pentamethylene-1-ethoxycarbonyl-2-(3',5'-dichlorophenyl thiocarbamoyl) hydrazine was instantaneously produced in a quantitative amount. A part of the reaction mixture was sampled and the solvent was removed therefrom to precipitate crystals; the melting point and elementary analysis thereof were as follows.

Melting point: 128°-130° C.

| Elementary analysis as $C_{15}H_{19}Cl_2N_3O_2S$: | | | | | |
|---|---|---|---|---|---|
|  | C% | H% | N% | Cl% | S% |
| Calculation | 47.88 | 5.09 | 11.17 | 18.84 | 8.52 |
| Found | 47.85 | 5.06 | 11.22 | 18.75 | 8.48 |

The reaction mixture containing the product as above was heated under reflux for 8 hours, allowed to cool and diluted with petroleum ether to precipitate crystals which were collected by filtration, washed with petroleum ether and recrystallized from ethanol/benzene to obtain 2.5 g of 1,2-pentamethylene-4-(3′,5′-dichlorophenyl) monothiourazole corresponding to a 77% yield.

Reference Example 5

Two grams of 3,5-dichlorophenyl isothiacyanate were added to a solution of 1.74 g of 1,2-tetramethylene-1-(ethylthio) thiocarbonyl in 10 ml of benzene with shaking, then there was observed precipitation of crystals of the following compound:

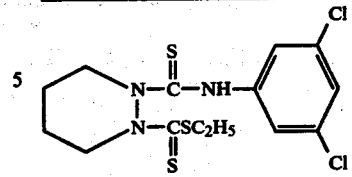

Melting point: 147°–149° C.
Elementary analysis as $C_{14}H_{17}Cl_2N_3S_3$:

|  | C% | H% | N% | Cl% | S% |
|---|---|---|---|---|---|
| Calculation | 42.63 | 4.35 | 10.65 | 17.98 | 25.39 |
| Found | 42.58 | 4.31 | 10.62 | 18.04 | 24.33 |

The reaction mixture containing the crystals was treated as in Reference Example 4 to obtain 2.4 g (the yield being 65%) of 1,2-tetramethylene-4-(3′,5′-dichlorophenyl) dithiourazole.

Various compounds which are suitable as active ingredient for the fungicide according to this invention are given in Table 1.

Table 1

| Compd. No. | Structure | Melting point (°C.) | C | H | N | Cl | S | Elementary assay (%) | Ref. Ex. |
|---|---|---|---|---|---|---|---|---|---|
| 1 | 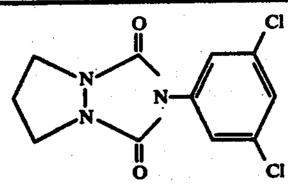 | 142 – 143.5 | 46.17<br>46.00 | 3.17<br>3.09 | 16.69<br>16.34 | 24.78<br>24.56 |  | $C_{11}H_9N_3Cl_2O_2$ | 1 |
| 2 | 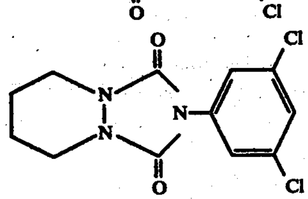 | 139 – 144 | 48.02<br>48.23 | 3.69<br>3.51 | 14.00<br>13.77 | 23.63<br>23.50 |  | $C_{12}H_{11}N_3Cl_2O_2$ | 2 |
| 3 | 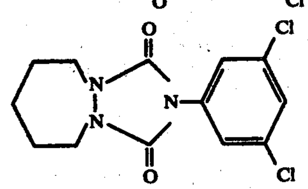 | 124 – 125 | 49.70<br>49.66 | 4.17<br>4.21 | 13.38<br>13.37 | 22.57<br>22.60 |  | $C_{13}H_{13}N_3Cl_2O_2$ | 1 |
| 4 | 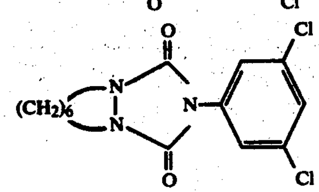 | 117 – 119 | 51.23<br>51.09 | 4.60<br>4.55 | 12.80<br>12.68 | 21.60<br>21.41 |  | $C_{14}H_{15}N_3Cl_2O_2$ | 1 |
| 5 | 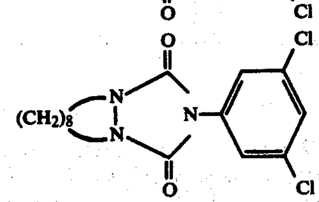 | 171 – 173 | 53.94<br>53.67 | 5.38<br>5.31 | 11.80<br>11.49 | 19.91<br>19.80 |  | $C_{16}H_{19}N_3Cl_2O_2$ | 1 |
| 6 | 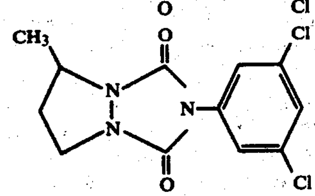 | 152 – 154 | 48.02<br>47.99 | 3.69<br>3.53 | 14.00<br>14.11 | 23.63<br>23.48 |  | $C_{12}H_{11}N_3Cl_2O_2$ | 1 |

Table 1-continued

| Compd. No. | Structure | Melting point(°C.) | Elementary assay (%) C | H | N | Cl | S | | Ref. Ex. |
|---|---|---|---|---|---|---|---|---|---|
| 7 | (structure) | 149 – 150 | 49.70 49.56 | 4.17 4.13 | 13.38 13.27 | 22.57 22.41 | | $C_{13}H_{13}N_3Cl_2O_2$ | 2 |
| 8 | (structure) | 167 | 49.70 49.63 | 4.17 4.08 | 13.38 13.25 | 22.57 22.42 | | $C_{13}H_{13}N_3Cl_2O_2$ | 2 |
| 9 | (structure) | 180 – 182 | 51.23 51.43 | 4.60 4.44 | 12.80 12.68 | 21.60 21.23 | | $C_{14}H_{15}N_3Cl_2O_2$ | 2 |
| 10 | (structure) | 246 – 248 | 51.23 51.58 | 4.60 4.28 | 12.80 12.64 | 21.60 21.60 | | $C_{14}H_{15}N_3Cl_2O_2$ | 2 |
| 11 | (structure) | 164 – 165.5 | 43.72 43.68 | 3.00 2.97 | 13.91 13.86 | 23.47 23.51 | 10.61 10.63 | $C_{11}H_9N_3Cl_2OS$ | 3 |
| 12 | (structure) | 199 – 200.5 | 45.58 45.44 | 3.51 3.60 | 13.29 13.21 | 22.43 22.19 | 10.14 10.00 | $C_{12}H_{11}N_3Cl_2OS$ | 4 |
| 13 | (structure) | 168 – 170 | 47.28 47.22 | 3.97 3.86 | 12.72 12.70 | 21.47 21.53 | 9.71 9.64 | $C_{13}H_{13}N_3Cl_2OS$ | 4 |
| 14 | (structure) | >250 | 43.38 43.29 | 3.34 3.30 | 12.65 12.58 | 21.34 21.33 | 19.30 19.27 | $C_{12}H_{11}N_3Cl_2S_2$ | 5 |

Note:
1 The figures in upper line are calculated and the figures in lower lines are found.
2 The compound was produced by the Reference Example set forth in the last column.

Among the compounds listed in Table 1, following compounds are found to be preferable as the active ingredient of the fungicide according to this invention:
1,2-(1″-methyl trimethylene)-4-(3′,5′-dichlorophenyl) urazole,
1,2-(1″-methyl tetramethylene)-4-(3′,5′-dichlorophenyl) urazole,
1,2-pentamethylene-4-(3′,5′-dichlorophenyl) monothiourazole.

Though 1,2-alkylene-4-(3′,5′-dichlorophenyl) urazole derivatives may be applied to plants as such as agricultural fungicides, it is convenient to use the compound diluted with a conventional adjuvant in the form of an emulsion, a wettable powder or a dust.

The adjuvant may be one which is conventionally used for formulating an agricultural fungicide, including a liquid or solid carrier, an emulsifier, a dispersing agent, a spreader, a penetrant and a surface active agent.

Examples of the liquid carrier which may be used according to this invention include a wide variety of solvents, for example, water, an alcohol such as methyl alcohol, ethyl alcohol or ethylene glycol; a ketone such as acetone, methyl ethyl ketone or cyclohexanone; an ether such as methyl ether, dioxane or cellosolve; an aliphatic hydrocarbon such as gasoline or kerosene; an aromatic hydrocarbon such as benzene, toluene, xylene, solvent naphtha or methyl naphthalene, a halogenated hydrocarbon such as dichloromethane, trichlorobenzene or carbon tetrachloride; an acid amide such as dimethylformamide; an ester such as ethylacetate, butylacetate, or a glyceride of an aliphatic acid; and a nitrile such as acetonitrile.

Examples of the solid carrier which may be used according to this invention include, for example, clay, koalin, bentonite, talc, diatomaceous earth, gypsum, vermiculite, alumina, sulfur, white carbon and carboxymethyl cellulose. Such solid carriers may be used alone or in a mixture of two or more.

Suitable surface active agents may be, for example, a nonionic type such as a polyoxyethylene alkylaryl ether and a polyoxyethylene sorbitol monolaurate; a cationic type such as an alkyl dimethylbenzyl ammonium chloride and an alkyl pyridinium chloride; an anionic type, such as an alkyl-benzene sulfonate, lignine sulfonate and a sulfate of a higher alcohol; and an amphoteric type, such as an alkyl dimethyl betaine and dodecylaminoethyl glycine.

Such adjuvants may be used alone or in a mixture of two or more.

The emulsion may be prepared by formulating 10 to 50 parts by weight of an active ingredient, 10 to 40 parts of a solvent and 5 20 parts of a surface active agent to form a concentrate which is diluted with water to a predetermined concentration and applied to the plant or soil by means of, for example, spray.

The wettable powder may comprise 10 to 50 parts by weight of an active ingredient, 10 to 40 parts of a solid carrier and 5 to 20 parts of a surface active agent. The powder may be used after diluting with water.

The dust may be a uniform mixture of 1 to 5 parts by weight of an active compound and 95 to 99 parts of a solid carrier.

The agricultural fungicides according to this invention may be used together with one or more other active ingredients which do not adversely affect fungicidal activity of the useful compound such as insecticide, miticide and other fungicide.

The fungicides according to this invention may be applicable to foliage and soil treatments and the effective dosage thereof is, in general, from 500 to 1500 ppm in case of foliage treatment and from 50 g to 300 g per 100 m² in case of soil treatment.

It has been found that the agricultural fungicides according to this invention possesses a wide fungicidal spectrum for preventing various plant diseases which are observed on fruits, such as apples and grapes, vegetables such as tomatoes and cucumbers, beans and rice plants including rice sheath blight disease, Botrysis gray mold disease, rice brown spot disease, Alternaria leaf spot and Sclerotinia spot. It has also been found that the fungicides are effective against two or more diseases simultaneously and show extremely low toxicity to humans and fish as well as low phytotoxicity.

This invention will be explained in detail by means of the following Example and Test Example; however, it should be understood that this invention is in no way limited by these Examples in which "parts" are by weight unless otherwise specifically limited.

Example 1 (Dust)

The following ingredients were mixed and pulverized to obtain a dust:
Compound No. 1: 3 parts
A mixture of clay and talc: 97 parts

Example 2 (Wettable powder)

The following ingredients were mixed and pulverized to prepare a wettable powder:
Compound No. 3: 20 parts
A mixture of clay and diatomaceous earth: 75 parts
Sodium alkylbenzene sulfonate: 3 parts
Polyoxyethylene nonylphenyl ether: 2 parts

Example 3 (Emulsion)

The following ingredients were mixed under agitation to prepare an emulsion.
Compound No. 2: 50 parts
Xylene: 40 parts
Polyoxyethylene nonylphenyl ether: 6 parts
Sodium alkylbenzene sulfonate: 4 parts

Test Example 1

Preventive Effect Against Rice Sheath Blight Disease

Rice plants (cultivar: Kinmaze), which were at the 5-6 leaf stage and were grown in 9 cm pots in a green house and cut at 20-30 cm height, were treated with suspensions of wettable powder of the chemicals at various concentrations in an amount of 20 ml per pot by spray application. After air drying, the plants were inoculated with pathogenic mycelia of *Pellicularia sasakii* which had been cultured on a wheat bran medium for seven days.

These pots were covered with cases made of polyvinyl chloride in order to prevent the escape of humidity and incubation was effected in a chamber maintained at a temperature of from 25° to 27° C. After twenty days, the rating on the disease severity index was determined.

On the other hand, procedures similar to the above were repeated but no chemical was applied to the rice plants.

Then, the preventive value of the chemicals was calculated according to the following equation.

Preventive value(%)=((A)−Disease severity index treated/Disease severity index untreated (being A))×100

The results are given in Table 2.

Table 2

| Compound No. | Preventive value (%) | | |
|---|---|---|---|
| | 1000 ppm | 500 ppm | 250 ppm |
| 2 | 100 | 98.6 | 89.2 |
| 3 | 100 | 97.3 | 88.4 |
| 5 | 92.1 | 85.3 | 76.4 |
| 6 | 99.0 | 95.3 | 86.6 |
| 7 | 85.4 | 72.3 | 65.8 |
| 8 | 99.4 | 91.2 | 84.6 |
| 9 | 83.4 | 72.0 | 61.5 |
| 10 | 79.4 | 75.8 | 63.0 |
| 11 | 98.6 | 92.4 | 89.6 |
| 12 | 90.8 | 83.7 | 70.0 |
| 13 | 91.4 | 86.3 | 72.5 |
| 14 | 97.4 | 93.2 | 85.3 |

Test Example 2

Preventive Effect Against Cucumber Gray Mold Disease

Cotyledons which were cut from cucumber seedlings (cultivar: Sagamihanziro) were dipped in aqueous suspensions of wettable powder having various concentrations of the chemicals and air dried. Pathogenic mycelia of *Botrytis cinerea* was inoculated on to the cotyledons and incubated in a humidity chamber maintained at 25° C. After 7 days, the rating on the disease severity index was determined.

On the other hand, procedures similar to the above were repeated but no chemical was applied to cotyledons.

Then, the preventive value was calculated according to the above equation.

The results are given in Table 3.

Table 3

| Compound No. | Preventive value (%) | | |
|---|---|---|---|
| | 1000 ppm | 500 ppm | 250 ppm |
| 1 | 100 | 98.0 | 92.1 |
| 2 | 96.4 | 92.3 | 88.5 |
| 3 | 100 | 95.7 | 90.4 |
| 4 | 86.2 | 82.4 | 72.3 |
| 6 | 92.5 | 86.4 | 80.8 |
| 10 | 85.3 | 79.0 | 68.4 |
| 11 | 98.6 | 89.3 | 82.1 |
| 12 | 85.3 | 80.4 | 73.8 |
| 14 | 91.6 | 85.0 | 72.9 |

Test Example 3

Protective Effect Against Kidney Bean Gray Mold Disease

Kidney beans plants of 2 leaf age were spray treated with suspensions of wettable powder of compounds to be tested in an amount of 25 ml and air dried.

Then, a 6 mm agar disc containing pathogenic mycelia of *Botrytis cinerea* was inoculated on to the leaves and incubated in a humidity chamber at 23° C. for 4 days.

Then, the protective value was calculated according to the equation given in Test Example 1.

The results are given in Table 4.

Table 4

| Compound No. | Protective value (%) |
|---|---|
| 1 | 100 |
| 2 | 96 |
| 3 | 89.7 |
| 4 | 78 |
| 6 | 100 |
| 7 | 93.3 |
| 8 | 72 |
| 12 | 75 |

What is claimed is:

1. A method of killing plant pathogenic fungi which comprises applying to said fungi a fungicidally effective amount of a compound represented by the following formula:

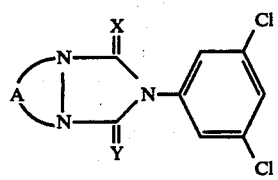

wherein each of X and Y represents oxygen or sulfur, and A represents alkylene having 4 carbon atoms which may have branched methyl.

2. The method of killing plant pathogenic fungi according to claim 1, wherein said compound is 1,2-tetramethylene-4-(3′,5′-dichlorophenyl) urazole.

3. The method of killing plant pathogenic fungi according to claim 1, wherein said compound is 1,2-(1″methyl tetramethylene)-4-(3′,5′-dichlorophenyl) urazole.

4. The method of killing plant pathogenic fungi according to claim 1, wherein said compound is 1,2-(2″-methyl tetramethylene)-4-(3′,5′-dichlorophenyl) urazole.

5. The method of killing plant pathogenic fungi according to claim 1, wherein said compound is 1,2-(2″,3″-dimethyl tetramethylene)-4-(3′,5′-dichlorophenyl) urazole.

6. The method of killing plant pathogenic fungi according to claim 1, wherein said compound is 1,2-(1″,4″-dimethyl tetramethylene)-4-(3′,5′-dichlorophenyl) urazole.

7. The method of killing plant pathogenic fungi according to claim 1, wherein said compound is 1,2-tetramethylene-4-(3′,5′-dichlorophenyl) thiourazole.

8. The method of killing plant pathogenic fungi according to claim 1, wherein said compound is 1,2-tetramethylene-4-(3′,5′-dichlorophenyl) dithiourazole.

* * * * *